United States Patent [19]

Au

[11] Patent Number: 5,036,154

[45] Date of Patent: Jul. 30, 1991

[54] PREPARATION OF GLYCIDYL ESTERS

[75] Inventor: Andrew T. Au, Sugarland, Tex.

[73] Assignee: The Dow Chemical Company, Midland, Mich.

[21] Appl. No.: 437,483

[22] Filed: Nov. 15, 1989

[51] Int. Cl.$^5$ ........................................... C07D 301/12
[52] U.S. Cl. ..................................................... 549/531
[58] Field of Search ......................................... 549/531

[56] References Cited

U.S. PATENT DOCUMENTS 3,335,156  8/1967  Smith ................................. 549/515

FOREIGN PATENT DOCUMENTS 0109273  5/1984  European Pat. Off. .
60-0122  4/1985  Japan .
56975    4/1985  Japan ................................... 549/531

OTHER PUBLICATIONS

"A New, Effective Catalytic ... ", *J. Org. Chem.*, vol. 48, pp. 3831–3833 (1983), by Venturello, Alneri and Ricci.

"Quaternary Ammonium Tetrakis ... ", *J. Org. Chem.*, vol. 53, pp. 1553–1557 (1988), by Venturello and D'Aloisio.

*Primary Examiner*—C. Warren Ivy
*Assistant Examiner*—Amelia A. Owens

[57] ABSTRACT

Glycidyl esters are prepared by reacting a compound containing one or more ethylenically unsaturated ester groups with hydrogen peroxide in the presence of an alkali metal or alkaline earth metal salt of tungstic acid, phosphoric acid and a phase transfer catalyst, optionally in the presence of one or more solvents.

19 Claims, No Drawings

PREPARATION OF GLYCIDYL ESTERS

FIELD OF THE INVENTION

The present invention pertains to the preparation of glycidyl esters, particularly polyglycidyl esters.

BACKGROUND OF THE INVENTION

Glycidyl esters, particularly polyglycidyl esters have been generally prepared by reacting carboxylic acids or di- or polycarboxylic acids with an epihalohydrin followed by dehydrohalogenation of the intermediate halohydrin product. In this method, often the product is oligomerized during the dehydrohalogenation step resulting in the product having a viscosity as well as an epoxide equivalent weight much higher than that desired. It would be desirable to have available a process for preparing glycidyl esters, particularly di- and polyglycidyl esters which have epoxide equivalent weight values substantially equivalent to the theoretical epoxide equivalent weight.

SUMMARY OF THE INVENTION

The present invention pertains to a process for preparing glycidyl esters which comprises reacting a compound containing one or more ethylenically unsaturated ester groups with hydrogen peroxide in the presence of (a) at least one alkali metal or alkaline earth metal salt of tungstic acid, (b) phosphoric acid and (c) at least one phase transfer catalyst.

DETAILED DESCRIPTION OF THE INVENTION

The reaction between the ethylenically unsaturated ester-containing compound and the hydrogen peroxide in the presence of the alkali metal or alkaline earth metal salt of tungstic acid, phosphoric acid and a phase transfer catalyst can be conducted at any temperature which is sufficient to cause reaction of the hydrogen peroxide with the unsaturated ester; however, particularly suitable temperatures include those from about 0° C. to about 100° C., preferably from about 25° C. to about 70° C., for a time sufficient to complete the reaction. Higher reaction temperatures require shorter reaction times whereas lower temperatures require longer reaction times. However, usually, the reaction is complete within about 24 to about 48 hours at a temperature of 40° C. to 45° C. At temperatures below about 0° C., the reaction will become very slow and the aqueous layer of the biphasic medium may freeze thereby causing difficulty in stirring. At temperatures above about 100° C., the hydrogen peroxide may undergo decomposition and the epoxy product may undergo hydrolysis.

The reaction can be conducted at pressures from subatmospheric to superatmospheric pressures; however, the reaction is most conveniently conducted at atmospheric pressure.

While it is not necessary, it is preferred that the reaction be conducted a biphasic manner in water and a suitable water immiscible organic solvent such as, for example, chlorinated hydrocarbons, aliphatic hydrocarbons, aromatic hydrocarbons, ethers, glycol ethers, combinations thereof and the like. Particularly suitable such solvents include, for example, toluene, chlorobenzene, chloroform, carbon tetrachloride, methylene chloride, diethyl ether, ethylene glycol di-n-butyl ether, ethylene glycol diethyl ether, ethylene glycol diphenyl ether, diethylene glycol di-n-butyl ether, diethylene glycol diethyl ether, butylene glycol dimethyl ether, dipropylene glycol diethyl ether, dipropylene glycol n-butyl ether, propylene glycol diethyl ether, propylene glycol dibutyl ether, propylene glycol diphenyl ether, any combination thereof and the like.

By the term "biphasic" it is meant that upon cessation of stirring, the reaction mixture will form two phases, an aqueous phase and an organic phase.

When employed, the organic solvents are present in amounts up to about 2,000, preferably up to about 1,000, more preferably from about 100 to about 400, percent by weight based upon the weight of the allyl ester.

In some instances, an organic reactant may act as its own solvent. In such instances, an organic solvent is not required, although one can be employed, if desired.

Suitable reactants which, when employed, do not require the presence of an organic solvent include, for example, diallyl glutarate, diallyl succinate, cyclohexane-1,2-dicarboxylic acid diallyl ester, and the like.

The hydrogen peroxide is suitably employed as an aqueous solution in concentrations of from about 5 to about 70, preferably from about 10 to about, 30 percent by weight.

The hydrogen peroxide is employed in amounts of from about 1 to about 10, preferably from about 1.5 to about 5, more preferably from about 1 5 to about 3, equivalents of hydrogen peroxide per equivalent of ethylenically unsaturated group present in the ester compound.

Suitable ethylenically unsaturated esters which can be employed herein include, for example any one or more of those represented by the following general formula I Formula I

wherein each R is independently an unsaturated aliphatic, unsaturated cycloaliphatic or aromatic hydrocarbon group having from 2 to about 30, preferably from about 2 to about 10, more preferably from about 3 to about 6, carbon atoms, or such unsaturated aliphatic, unsaturated cycloaliphatic or aromatic hydrocarbon groups containing hydroxyl, alkoxy, nitro, halogen, carbonyl or the like substituents; each Z is independently a single bond, a mono-, di- or polyvalent saturated aliphatic, saturated cycloaliphatic or aromatic organic moiety having from about 1 to about 20, preferably from about 1 to about 15, more preferably from about 2 to about 12, carbon atoms or such moieties substituted with hydroxyl, alkoxy, nitro, halogen, carbonyl or the like groups; and x has a value from 1 to about 4, preferably 2 or 3, more preferably 2. Particularly suitable such esters include, for example, diallyl glutarate, diallyl sebaccate, diallyl terephthalate, diallyl succinate, allyl esters of cyclohexane di- or tri-carboxylic acids, naphthalene di- or tri-carboxylate allyl esters, any combination thereof and the like.

Suitable alkali metal or alkaline earth metal salts of tungstic acid which can be employed herein include, for example, sodium tungstate dihydrate, potassium tungstate dihydrate, lithium tungstate dihydrate, magnesium tungstate, any combination thereof and the like. Particularly suitable such salts of tungstic acid include, for example, sodium tungstate dihydrate, potassium tungstate, dihydrate, lithium tungstate dihydrate, any combination thereof and the like.

The alkali metal or alkaline earth metal salt of tungstic acid is employed in amounts which provides from about 0.001 to about 1, preferably from about 0.001 to about 0.01, more preferably from about 0.01 to about 0.05, equivalent of tungstic acid salt per equivalent of allyl ester.

Suitable phase transfer catalysts which can be employed herein include, for example, those represented by the following general formula II Formula 11

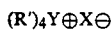

wherein each R' is independently a hydrocarbyl group or a hydroxyl, alkoxy, halogen or nitro substituted hydrocarbyl group having from 1 to about 40 carbon atoms with the proviso that the sum of the carbon atoms contained in the R' groups is from about 16 to about 40, Y is nitrogen or phosphorus and X is the anion portion of an inorganic acid. Particularly suitable phase transfer catalysts include, for example, trioctylmethylammonium chloride, trioctylmethylammonium bromide, trioctylmethylammonium nitrate, trioctylmethylammonium hydrogen sulfate, tetrahexylammonium chloride, tetrahexylammonium bromide, tetrahexylammonium nitrate, tetrahexylammonium hydrogen sulfate, tetrabutylammonium chloride, tetrabutylammonium bromide, tetrabutylammonium nitrate, tetrabutylammonium hydrogen sulfate, dioctadecyldimethylammonium chloride, dioctadecyldimethylammonium bromide, dioctadecyldimethylammonium nitrate, dioctadecyldimethylammonium hydrogen sulfate, dihexadecydimethylammonium chloride, dihexadecydimethylammonium bromide, dihexadecydimethylammonium nitrate, dihexadecydimethylammonium hydrogen sulfate, trioctylmethylphosphonium chloride, trioctylmethylphosphonium bromide, trioctylmethylphosphonium nitrate, trioctylmethylphosphonium hydrogen sulfate, tetrahexylphosphonium chloride, tetrahexylphosphonium bromide, tetrahexylphosphonium nitrate, tetrahexylphosphonium hydrogen sulfate, tetrabutylphosphonium chloride, tetrabutylphosphonium bromide, tetrabutylphosphonium nitrate, tetrabutylphosphonium hydrogen sulfate, dioctadecyldimethylphosphonium chloride, dioctadecyldimethylphosphonium bromide, dioctadecyldimethylphosphonium nitrate, dioctadecyldimethylphosphonium hydrogen sulfate, dihexadecydimethylphosphonium chloride, dihexadecydimethylphosphonium bromide, dihexadecydimethylphosphonium nitrate, dihexadecydimethylphosphonium hydrogen sulfate, any combination thereof and the like.

The phase transfer catalyst is employed in amounts which proved from about 0.001 to about 1, preferably from about 0.001 to about 0.2, more preferably from about 0.005 to about 0.05, equivalents of phase transfer catalyst per equivalent of allyl ester.

Phosphoric acid is employed, as a complexing agent for the tungstic acid salt, in an amount which provides from about 0.1 to about 1, preferably from about 0.001 to about 0.02, more preferably from about 0.02 to about 0.1 equivalents of phosphoric acid per equivalent of allyl ester.

If desired, additional quantities of phosphoric acid is employed to adjust the pH of the reaction mixture so as to bring it into a range of from about 0.1 to about 5, preferably from about 1 to about 3.5. Other acids can be employed for adjusting the pH of the reaction mixture instead of additional quantities of phosphoric acid. Such acids include, for example, inorganic mineral acids or strong organic acids. Particularly suitable are sulfuric acid, hydrochloric acid, hydrobromic acid, nitric acid, perchloric acid, p-toluene sulfonic acid, methane sulfonic acid, trifluoracetic acid, tribromoacetic acid, trichloroacetic acid, combinations thereof and the like.

The di- and polyglycidyl esters prepared by the present invention can be employed in coatings, castings, laminates, electrical potting/encapsulation, molding, composites, adhesives, and the like.

The following examples are illustrative of the invention, but are not to be construed as to limiting the scope thereof in any manner.

EXAMPLE 1

Preparation of Diglycidyl Terephthalate

An aqueous solution of pH 2.1, formed from 330 mg of sodium tungstate dihydrate, 200 mg of 85% phosphoric acid and 1.2 ml (25 m equiv.) of 70% hydrogen peroxide in 5 ml of water, is added to an organic lyl terephthalate solution of 1.23 g (2.5 equiv.) of dial and 200 mg of trioctylmethylammonium chloride in 7 ml of toluene. After stirring at 45° C. over the weekend, gas chromatography (GC) shows that the reaction has proceeded cleanly to completion. The organic layer is separated, washed with water, dried over magnesium sulfate and concentrated to a light colored oil in the amount of 1.36 g. The yield is 85% based on diallyl terephthalate. Both nuclear magnetic resonance (NMR), infra red spectrum (IR) and GC show this material to be the desired diglycidyl terephthalate. {IR:1718 cm$^1$; NMR: $\delta$2.8 (4H, m), $\delta$3.4 (2H, m), $\delta$4.0–4.8 (4H. m) and $\delta$8.2 (4H, s)}.

EXAMPLE 2

Preparation of Diglycidyl Glutarate

An aqueous solution of pH 2.1, formed from 330 mg of sodium tungstate dihydrate, 200 mg of 85% phosphoric acid and 1.2 ml (24.7 m equiv.) of 70% hydrogen peroxide in 5 ml of water, is added to an organic solution of 1.23 g (2.5 equiv.) of diallyl glutarate and 200 mg of trioctylmethylammonium chloride in 7 ml of toluene. After stirring at 45° C. over the weekend, gas chromatography (GC) shows that the reaction has proceeded cleanly to completion. The organic layer is separated, washed with water, dried over magnesium sulfate and concentrated to a light colored oil in the amount of 1.36 g. The yield is 94% based on diallyl glutarate. {IR data: 1726 cm$^1$: NMR data: $\delta$2.6–3.05, m(4H), $\delta$3.1–3.45, m(2H), $\delta$3.8–4.8, m(4H) and $\delta$8.1, s(4H)}.

What is claimed is:

1. A process for preparing glycidyl esters which comprises reacting a compound or mixture of compounds containing one or more ethylenically unsaturated ester groups with hydrogen peroxide in the presence of (a) at least one alkali metal or alkaline earth metal salt of tungstic acid, (b) phosphoric acid and (c) at least one phase transfer catalyst.

2. A process of claim 1 wherein
   (a) said hydrogen peroxide is employed in an amount of from about 1 to about 10 equivalents per equivalent of ethylenically unsaturated ester;

(b) said alkali metal or alkaline earth metal salt of tungstic acid is present in an amount of from about 0.001 to about 1 equivalent per equivalent of unsaturated ester:

(c) said phase transfer catalyst is present in an amount of from about 0.001 to about 1 equivalent of phase transfer catalyst per equivalent of unsaturated ester;

(d) said phosphoric acid is present in an amount which provides from about 0.001 to about 1 equivalent of phosphoric acid per equivalent of unsaturated ester; and (e) the reaction mixture is adjusted to a pH of from about 0.1 to about 5 with any suitable acid.

3. A process of claim 1 wherein (a) said hydrogen peroxide is employed in an amount of from about 1.5 to about 5 equivalents per equivalent of ethylenically unsaturated ester;

(b) said alkali metal or alkaline earth metal salt of tungstic acid is present in an amount of from about 0.001 to about 0.02 equivalent per equivalent of unsaturated ester;

(c) said phase transfer catalyst is present in an amount of from about 0.001 to about 0.2 equivalent of phase transfer catalyst per equivalent of unsaturated ester and (d) said phosphoric acid is present in an amount which provides from about 0.01 to about 0.2 equivalent of phosphoric acid per equivalent of unsaturated ester; and (e) the reaction mixture is adjusted to a pH of from about 1 to about 3.5 with any suitable acid.

4. A process of claim 1 wherein (a) said hydrogen peroxide is employed in an amount of from about 1.5 to about 3 equivalents per equivalent of ethylenically unsaturated ester;

(b) said alkali metal or alkaline earth metal salt of tungstic acid is present in an amount of from about 0.02 to about 0.1 equivalent per equivalent of unsaturated ester:

(c) said phase transfer catalyst is present in an amount of from about .005 to about 0.05 equivalent of phase transfer catalyst per equivalent of unsaturated ester; and (d) said phosphoric acid is present in an amount which provides from about 0.02 to about 0.1 equivalent of phosphoric acid per equivalent of unsaturated ester.

5. A process of claim 1, 2, 3 or 4 wherein (a) said compound containing one or more ethylenically unsaturated ester groups is a compound represented by the following general formula I Formula 1

wherein each R is independently an unsaturated aliphatic, unsaturated cycloaliphatic or aromatic hydrocarbon group containing from about 2 to about 30 carbon atoms or such unsaturated aliphatic, unsaturated cycloaliphatic or aromatic hydrocarbon group containing hydroxyl, alkoxy, nitro, halogen, carbonyl or the like substituents; each Z is independently a single bond, a mono-, di- or polyvalent aliphatic or aromatic organic moiety having from about 1 to about 12 carbon atoms or such moieties substituted with hydroxyl, alkoxy, nitro, halogen, carbonyl or the like groups: and x has a value from 1 to about 4; and (b) said phase transfer catalyst is a compound represented by the following general formula II Formula II

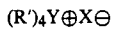

wherein each R' is independently a hydrocarbyl group or a hydroxyl, alkoxy, halogen or nitro substituted hydrocarbyl group having from 1 to about 40 carbon atoms with the proviso that the sum of the carbon atoms contained in the R' groups is from about 16 to about 40, Y is nitrogen or phosphorus and X is the anion portion of an inorganic acid.

6. A process of claim 5 wherein (a) said alkali metal or alkaline earth metal salt of tungstic acid is sodium tungstate dihydrate, potassium tungstate dihydrate, lithium tungstate dihydrate, or any combination thereof;

(b) in formula I, each R is independently an unsaturated aliphatic hydrocarbon group having from about 2 to about 10 carbon atoms or such unsaturated aliphatic hydrocarbon group containing hydroxyl, alkoxy, nitro, halogen, carbonyl or the like substituents; each Z is independently a single bond, a mono-, dior polyvalent aliphatic or aromatic organic moiety having from about 1 to about 15 carbon atoms or such moieties substituted with hydroxyl, alkoxy, nitro, halogen, carbonyl groups; and X has a value from of 2 or 3: and (c) in formula II, X is chloride, bromide, nitrate, sulfate, hydrogen sulfate, perchlorate, phosphate, or sulfonate.

7. A process of claim 5 wherein (a) aid alkali metal or alkaline earth metal salt of tungstic acid is sodium tungstate dihydrate, or potassium tungstate dihydrate:

(b) sin formula I, each R is independently an unsaturated aliphatic hydrocarbon group having from about 3 to about 6 carbon atoms or such unsaturated aliphatic hydrocarbon group containing hydroxyl, alkoxy, nitro, halogen, carbonyl or the like substituents; each Z is independently a mono-, dior polyvalent aliphatic or aromatic organic moiety having from about 1 to about 12 carbon atoms or such moieties substituted with hydroxyl, alkoxy, nitro, halogen, carbonyl groups; and x has a value of 2; and (c) in formula II, X is bromide, chloride, nitrate, sulfate, or hydrogen sulfate, phosphate, perchlorate and sulfonate.

8. A process of claim 1, 2, 3 or 4 wherein the reaction is conducted in the presence of water and at least one organic solvent.

9. A process of claim 8 wherein said organic solvent is an aromatic hydrocarbon, a halogenated aliphatic or aromatic hydrocarbon, or any combination thereof.

10. A process of claim 9 wherein said organic solvent is toluene, benzene, xylene, chloroform, methylene chloride, carbon tetrachloride, chlorobenzene, or any combination thereof.

11. A process of claim 5 wherein the reaction is conducted in the presence of water at least one organic solvent.

12. A process of claim 11 wherein said organic solvent is an aromatic hydrocarbon, a halogenated aliphatic or aromatic hydrocarbon, or any combination thereof.

13. A process of claim 12 wherein said organic solvent is toluene, benzene, xylene, chloroform, methylene chloride, carbon tetrachloride, chlorobenzene, or any combination thereof.

14. A process of claim 6 wherein the reaction is conducted in the presence of water and at least one organic solvent.

15. A process of claim 14 wherein said organic solvent is an aromatic hydrocarbon, a halogenated aliphatic or aromatic hydrocarbon, or any combination thereof.

16. A process of claim 15 wherein said organic solvent is toluene, benzene, xylene, chloroform, methylene chloride, carbon tetrachloride, chlorobenzene, or any combination thereof.

17. A process of claim 7 wherein the reaction is conducted in the presence of water and at least one organic solvent.

18. A process of claim 17 wherein said combination thereof.

19. A process of claim 18 wherein said organic solvent is toluene, benzene, xylene, chloroform, methylene chloride, carbon tetrachloride, chlorobenzene, or any combination thereof.

* * * * *

UNITED STATES PATENT AND TRADEMARK OFFICE
CERTIFICATE OF CORRECTION

PATENT NO. : 5,036,154
DATED : July 30, 1991
INVENTOR(S) : Andrew T. Au

It is certified that error appears in the above-identified patent and that said Letters Patent is hereby corrected as shown below:

Col. 5, line 4; change the colon ":" to a semicolon --;--.

Col. 5, line 26; after "ester" add a semicolon --;--.

Col. 5, line 41; after "ester", change the colon ":" to a semicolon --;--.

Col. 6, line 1; change the colon ":" to a semicolon --;--.

Col 6, line 28; change "a mono-, dior polyvalent" to read -- a mono-, di- or polyvalent--.

Col. 6, line 32; change "of 2 or 3:and" to read --of 2 or 3; and--.

Col. 6, line 45, change "mono-, dior" to read --mono-, di or--.

Col. 8, line 8; change "wherein said combination" to read --wherein said organic solvent is an aromatic hydrocarbon, a halogenated aliphatic or aromatic hydrocarbon or any combination--.

Signed and Sealed this

Sixth Day of July, 1993

Attest:

MICHAEL K. KIRK

Attesting Officer

Acting Commissioner of Patents and Trademarks